United States Patent [19]

Plessers

[11] 4,358,948
[45] Nov. 16, 1982

[54] METHOD AND APPARATUS FOR PREDICTING METALLOGRAPHIC STRUCTURE

[75] Inventor: Jacques Plessers, Houthalen, Belgium

[73] Assignee: Electro-Nite Co., Philadelphia, Pa.

[21] Appl. No.: 903,349

[22] Filed: May 5, 1978

[30] Foreign Application Priority Data

May 18, 1977 [FR] France .................................. 77 15402

[51] Int. Cl.³ ............................................ G01N 25/04
[52] U.S. Cl. .................................. 374/26; 73/DIG. 9; 374/16
[58] Field of Search .......... 73/17 R, 354, 359, DIG. 9

[56] References Cited

U.S. PATENT DOCUMENTS

| | | | |
|---|---|---|---|
| 3,321,973 | 5/1967 | Anderson | 73/359 |
| 3,559,452 | 2/1971 | Perbix et al. | 73/17 |
| 3,598,576 | 8/1971 | Moore et al. | 75/130 |
| 3,748,908 | 7/1973 | Falk | 73/17 |
| 3,813,944 | 6/1974 | Ryntz, Jr. et al. | 73/17 X |
| 4,008,604 | 2/1977 | Roach et al. | 73/17 |

FOREIGN PATENT DOCUMENTS 1090603  5/1966  United Kingdom ..................... 73/15

*Primary Examiner*—Herbert Goldstein
*Attorney, Agent, or Firm*—Seidel, Gonda, Goldhammer and Panitch

[57] ABSTRACT

A metallographic structure such as nodularity in castings to be made from molten metal is predicted by causing one part of the sample to rapidly solidify at a first rate and a second part of the sample to solidify at a slower rate. The temperature of at least said one part of the sample is measured during solidification. After solidification of the one part of the sample, the heat conductivity of the sample is used to predict the metallographic structure of the sample.

16 Claims, 7 Drawing Figures

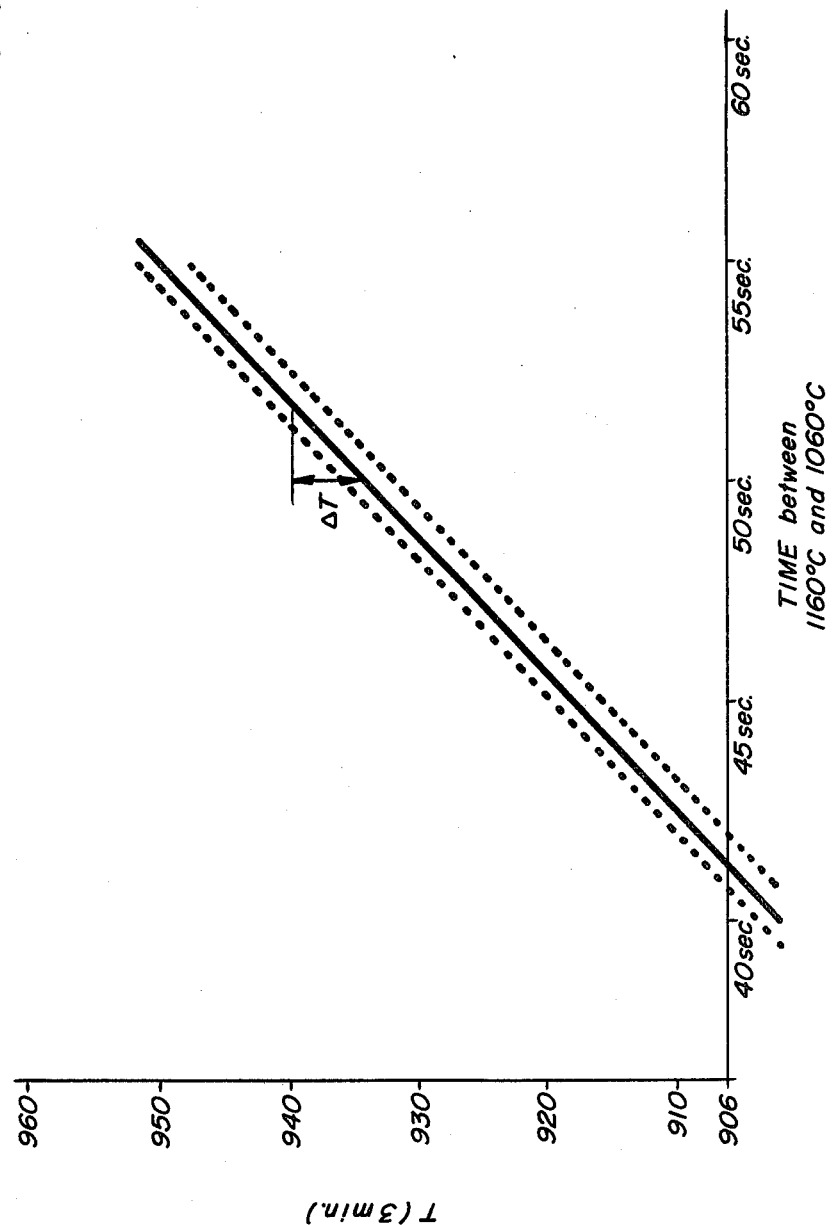

METHOD AND APPARATUS FOR PREDICTING METALLOGRAPHIC STRUCTURE

BACKGROUND

The present invention relates generally to a process for rapidly predicting a metallographic structure, such as the degree of nodularity, of castings to be made from molten metal before casting and apparatus for performing the same.

It is known that the composition of molten metal may be estimated by recording the liquidus and eutectic temperatures using known cooling curves. Such method provides information such as a change in phase, carbon equivalent, etc. It is also known to determine the thermal conductivity of solid bodies by measuring the heat flow through such body when subjected to a thermal gradient.

It has been observed that in grey cast iron in the solid state, the thermal conductivity is substantially influenced by the graphitic structure and that a nodular cast iron, for instance, has a lower conductivity than a lamellar or equivalent composition.

When pouring cast iron, it is important that analysis be carried out very quickly and before casting. If one waits too long before completing a pour of a nodular cast iron, a large percentage of the magnesium which is present in the molten metal will dissipate or will otherwise be lost and there is a likelihood of making an unsatisfactory cast.

The industry has long sought a simple, rapid and effective way of accurately predicting the degree of nodularity of a cast iron before casting of the same. One method proposed heretofore is disclosed in U.S. Pat. No. 3,670,558 wherein the properties of a nodular cast iron are evaluated by way of a comparative study of conventional cooling curves and a set or family of curve segments. The method proposed by said patent has not proven to be acceptable.

Thus, at the present time, the degree of nodularity of a cast iron can only be determined with precision if the sample is cooled and evaluated by ultrasonic or metallographic analysis, and the like.

The main object of the present invention is to cope with said problem by proposing a new process and apparatus making it possible to predict in a simple, rapid and effective manner the degree of nodularity of the cast iron casting while the iron is still molten and while it is still possible to change the composition of the molten metal or it is possible to scrap the molten metal.

SUMMARY OF THE INVENTION

The process of the present invention is directed to predicting a metallographic structure of a casting which will result from use of a molten metal and comprises the steps of obtaining a sample of the molten metal; causing one part of the sample to solidify at a first rate and a second part of the sample to solidify at a slower rate; ascertaining a parameter of heat conductivity, and using the heat conductivity parameter of the sample after solidification of the first part to determine the metallographic structure which would result from use of the molten metal.

Apparatus for accomplishing the method described above includes a small crucible into which a sample of molten metal is poured and within which the sample cools. The crucible in one embodiment has two temperature sensing devices at spaced locations corresponding to the first and second parts of the sample. In the preferred embodiment of the crucible, there is only one temperature sensing device. A means is associated with each of the types of crucibles to cause one part of the sample to solidify at a faster rate.

It is an object of the present invention to provide apparatus and method which will facilitate predicting in a simple, rapid and reliable manner the degree of nodularity or other metallographic structure which will be present in a casting made from a particular batch of cast iron.

Other objects will appear hereinafter.

For the purpose of illustrating the invention, there is shown in the drawings a form which is presently preferred; it being understood, however, that this invention is not limited to the precise arrangements and instrumentalities shown.

FIG. 6 is a graph of temperature after 3 minutes versus temperature to cool through a 100° C. zone containing the solidus arrest of the sample.

Figure 1:
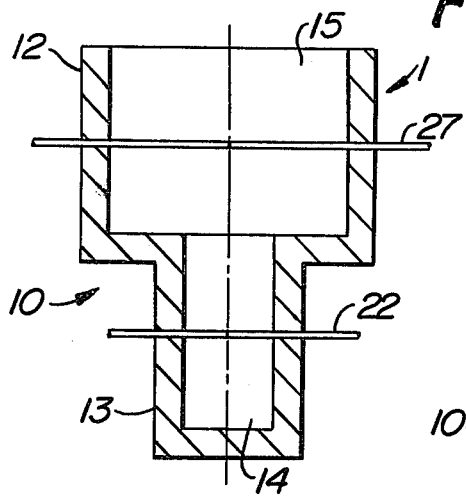
FIG. 1 is a sectional view through a first type of crucible usable in practicing the method of the present invention.

Referring to the drawings in detail, wherein like numerals indicate like elements, there is shown in FIG. 1 a first form of apparatus for use in practicing the method of the present invention. Thus, there is shown a crucible designated generally as 10, the diameter of the upper part 12 being much greater than the diameter of the lower part 13. As used herein, the word crucible is intended to include sample cups, molds used for IN-MOLD processes, and the like. A crucible 10 constructed in this manner makes it possible to cool a sample of molten metal at two different rates. Thus, the lower portion 14 of a sample in the crucible 10 will cool more rapidly than the upper portion 15 of the sample in crucible 10 because the ratio of surface area to volume of the upper portion is smaller than that of the lower portion.

Figure 2:
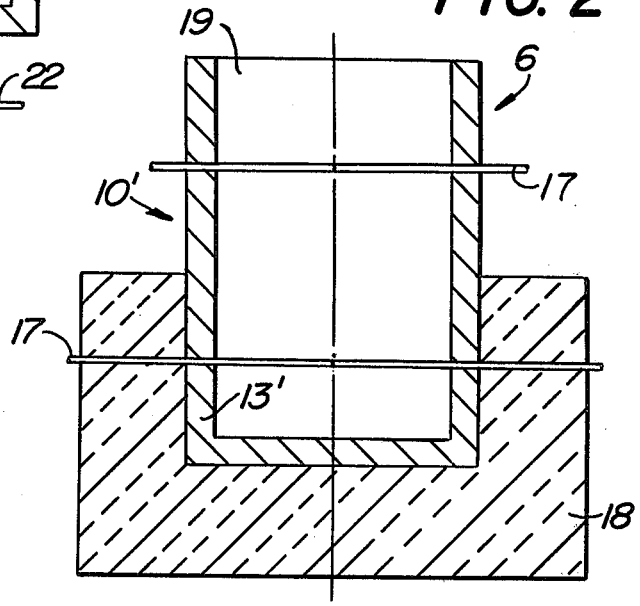
FIG. 2 is a sectional view through another type of crucible usable when practicing the method of the present invention.
Figure 5:
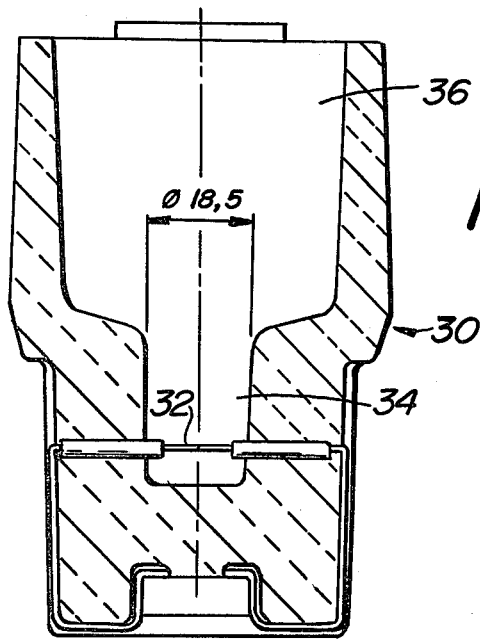
FIG. 5 is a sectional view through another crucible.

In FIG. 2, there is illustrated a second form of apparatus for use in practicing the method of the present invention. In FIG. 2, there is shown a crucible 10' of constant diameter and containing thermocouples 17,17'. The lower portion 13' of the crucible 10' is placed in a jacket 18 of heat insulating material. As a result of the jacket 18, the portion of the sample in the upper portion 19 of the crucible 10' will solidify at a faster rate as compared with the rate of solidification of the sample in the lower portion of the crucible 10'.

Although the crucibles 10 and 10' are slightly different in construction as to their contour, the principle utilized in the method of the present invention is the same. In order to prevent the formation of shrinkage cavities in the sample, it is preferable to design the crucibles in such a way that the portion having the fastest rate of solidification is in the lower portion of the crucible. Hence, the following description with respect FIG.

3 will only make reference to crucible 10 shown in FIG. 1.

Figure 3:
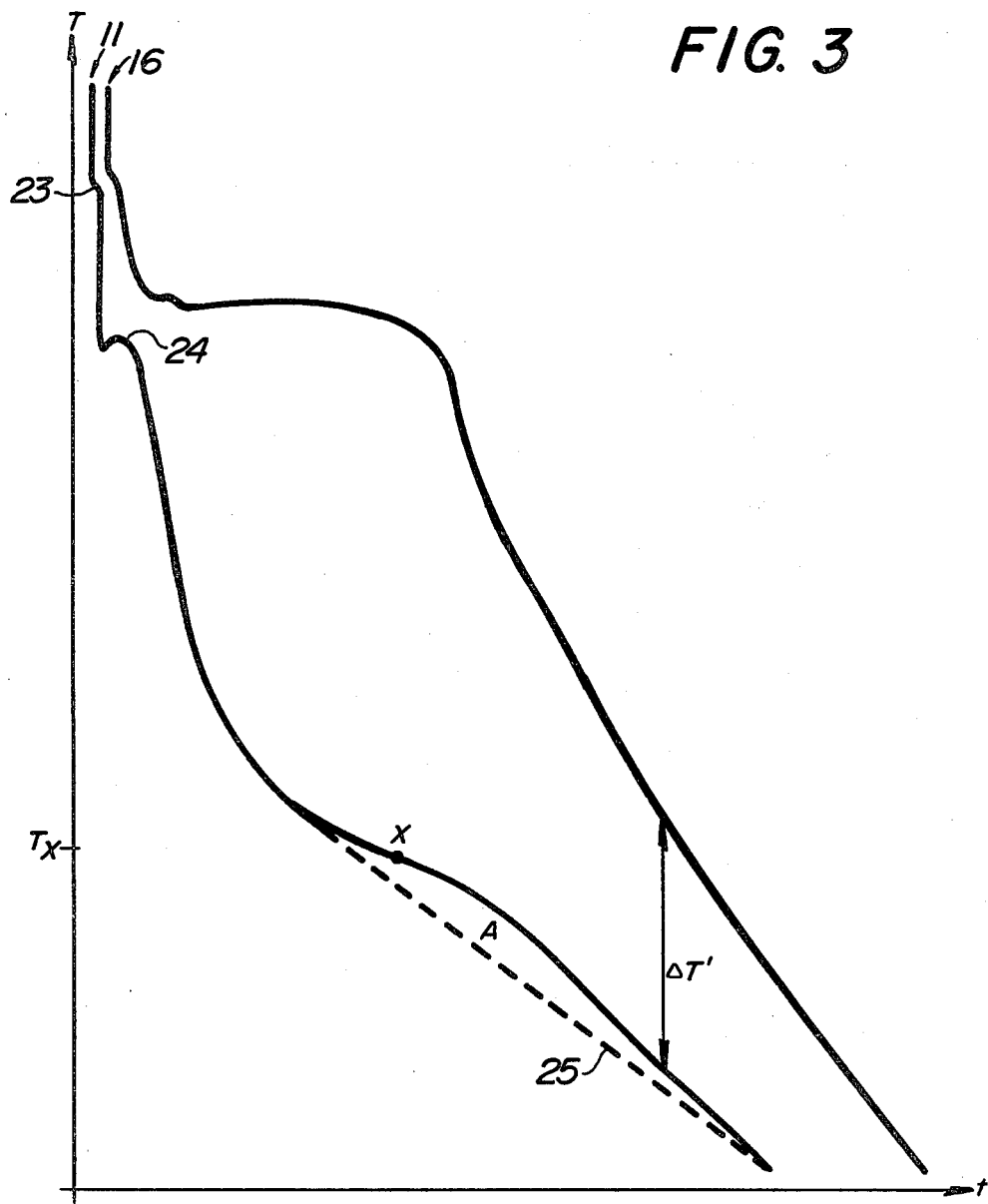
FIG. 3 is a graph showing two cooling curves showing temperature plotted against time.

FIG. 3 represents the solidification curve 11 of portion 14 of a sample of grey cast iron at a first rate of cooling. The temperature of the sample in portion 14 is sensed by a thermal sensing element such as thermocouple 22. The thermocouple 22 is, in a preferred embodiment, generally perpendicular to the center line or axis of the crucible 10. It will be seen from the curve 11 that a change in cooling rate at point 23 is recorded and corresponds to the liquidous temperature. There is also a more pronounced temperature change at point 24 corresponding to the solidous temperature. Thereafter curve 11 shows an inflection at a temperature $T_X$ instead of continuing to cool exponentially along the line 25 as would be the case in an ordinary solidification curve in the case of a homogeneous cooling of the sample.

In the present case, the inflection of the curve 11 at point X is caused by the thermal reflection during the eutectic solidification of the upper portion 15 of the sample cooling at a second and lower rate as compared with the rate of cooling of the portion 14. The temperature $T_X$ is the temperature at the point of inflection X on the curve 11. The temperature $T_X$ is a first parameter which is directly related to the thermal conductivity of the molten metal. The change in cooling rate results from the temperature of the eutectic level stretch of line 16 remaining practically constant around 1150° C.

Curve 11 and line 25 delimit an area A which is also directly related to the thermal conductivity of the sample. That is, the area A represents the thermal influence of the eutectic of portion 15 of the sample on portion 14 of the sample. It has been noted that the thermal conductivity is related to the metallographic structure of a metal. A reading of temperature $T_X$ which relates to the point of inflection in the curve 11 and/or the evaluation of the area A, are related to the metallographic structure of the metal sample being analyzed.

The two parameters mentioned above can also be checked when the solidification curve 16 of the sample is recorded at the same time on a single graph along with curve 11. To obtain the solidification curve 16, a temperature sensor such as a second thermocouple 27 is provided in the crucible 10 at a location which is associated with portion 15 of the sample. Thus, the thermocouples 22 and 27 are at substantially different locations but each is associated with one portion of the sample. At any given time, the diference in temperature between the two curves 11 and 26 varies with the conductivity of the metal sample and consequently with its degree of nodularity. Hereinafter, such temperature difference will be referred to as $\Delta T'$.

It has been ascertained that $T_X$ is influenced by the eutectic temperature of portion 15 and a number of other factors including thermal conductivity, pouring temperature, the manner of pouring. It is desired to determine the thermal conductivity of the sample. It is thus desirable to eliminate the influence of the other parameters. If the thermocouple 22 is at about the eutectic temperature of portion 14, cooling rate is not influence to any significant extent by thermal conductivity since thermal gradiants are relatively low. This makes possible the determination of a parameter "normal cooling rate" which is a rate without substantial influences of thermal conductivity. In this example, this rate is defined as the rate of cooling across the 100° C. range between 1160° C. to 1060°. It is further convenient to use a temperature which is related to $T_X$ such as the temperature of the iron sample exactly 3 minutes after start of pouring. Other periods of time could be used or other techniques could be used to establish "normal cooling rate" such as a first derivative of the cooling curve at a point where thermal conductivity plays a minor role such as a point near the eutectic temperature. Furthermore, other parameters derived from the cooling curve can be used in place of $T_X$ such as the time required to reach a prescribed temperature which is suitably lower than the eutectic, or the first derivative of the cooling curve at a certain time or temperature, can be satisfactorily related to thermal conductivity.

Figure 4:
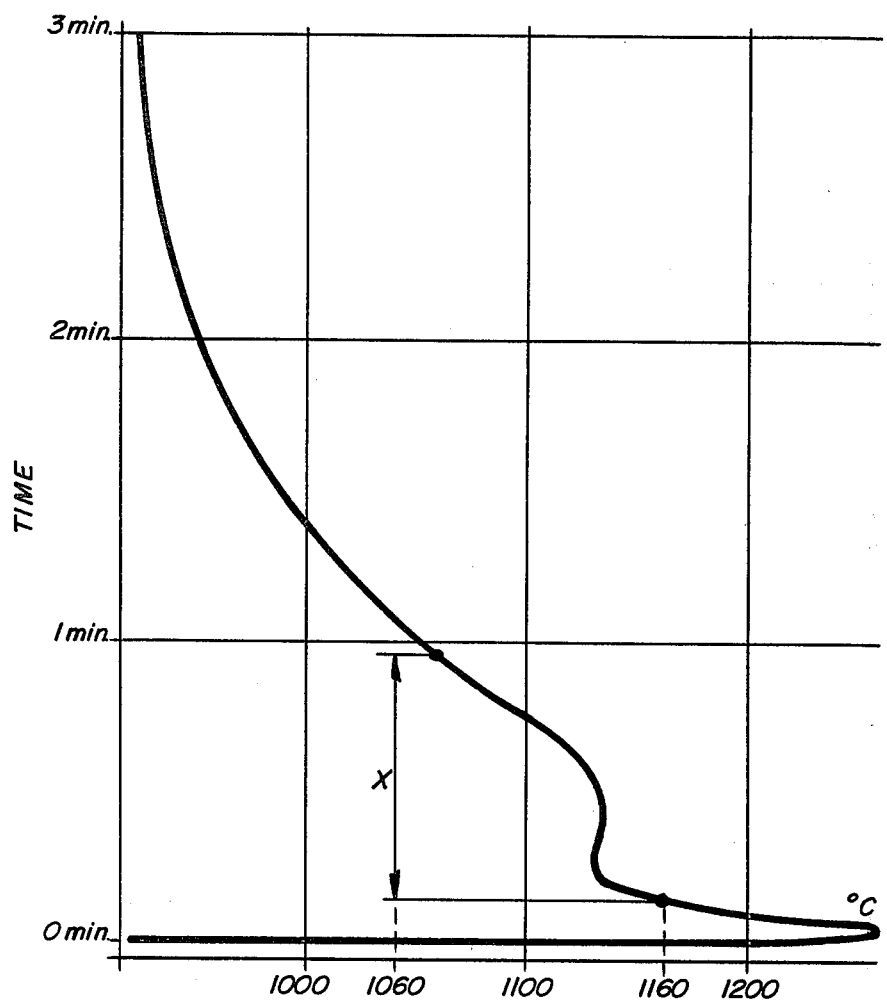
FIG. 4 is a graph showing a cooling curve wherein temperature is plotted against time using a single thermocouple.

Another embodiment of this invention is to use crucible 10 without thermocouple 27, namely crucible 30. In FIG. 4, there is shown a cooling curve of time versus temperature obtained from a sample of cast iron cooled in crucible 30. In FIG. 4, the designation "X" indicates the time to cool through the 100° C. range from 1160° C. to 1060° C.

Crucible 30 is similar to crucible 10 but only contains a single alumel-chromel thermocouple 32 within lower portion 34. Crucible 30 has a larger portion 36 coextensive with portion 34. Typical dimensions for portion 34 are diameter of 18.5 mm; height 29 mm; and thermocouple 32 spaced from the bottom of portion 34 by 6 mm. Typical dimensions for portion 36 are diameter of 50 mm and a height of 46 mm. For the reasons described above, that part of the sample in portion 34 will cool at a faster rate than the part of the sample in portion 36. A crucible as disclosed in U.S. Pat. No. 4,056,407 can be modified to have the features of crucible 30.

FIG. 6 is a graph wherein the temperature of the sample as read by the thermocouple 32 at the end of 3 minutes is plotted against time in seconds for the sample to cool from 1160° C. to 1060° C. The graph of FIG. 6 has been experimentally determined to define the time temperature relationship of suitable nodular iron when poured into a specific crucible. From FIG. 4, the temperature is 938° C. and the time "X" is 50 seconds. When these parameters are applied to FIG. 6, $\Delta T$ is 4° C.

Figure 7:
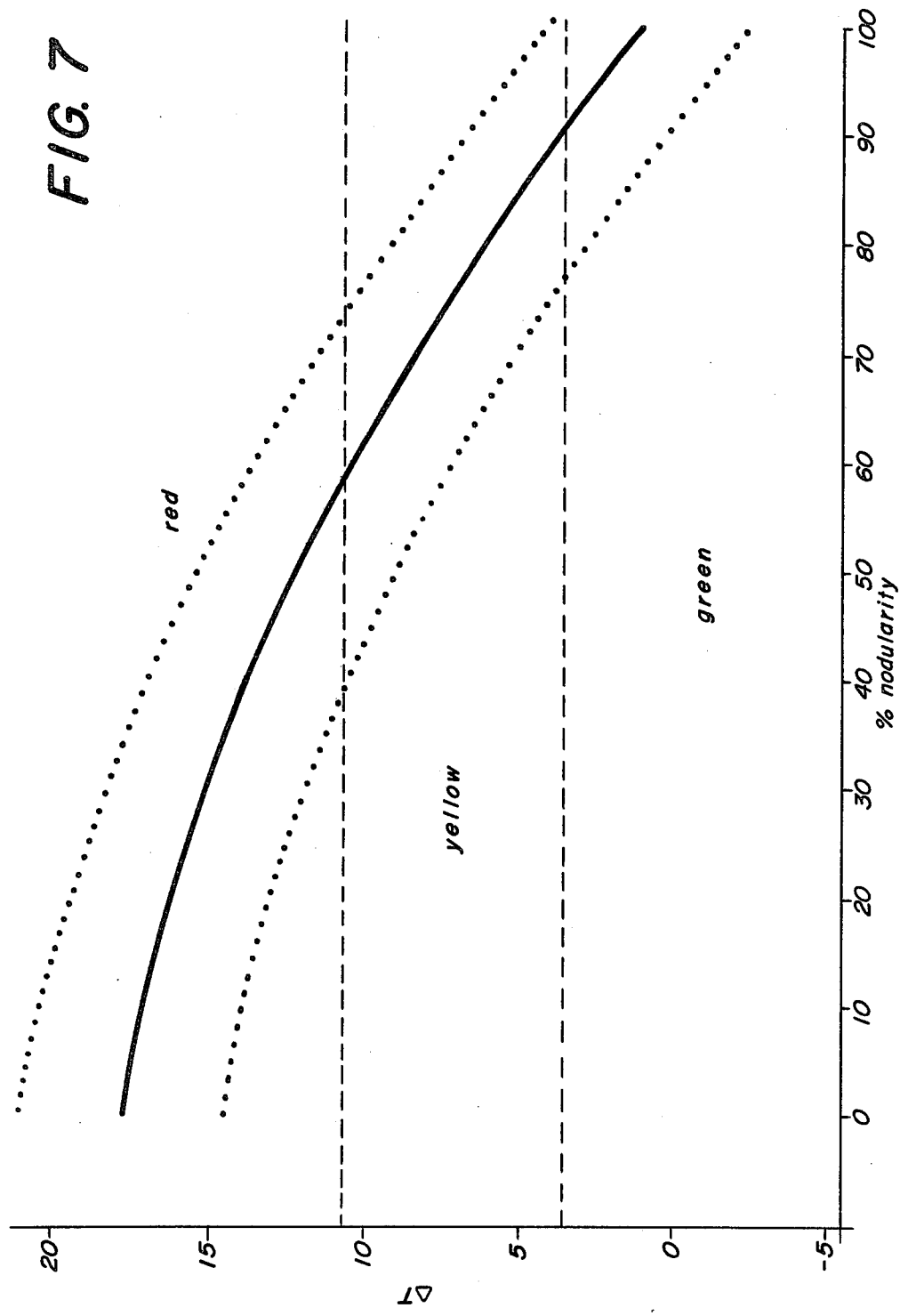
FIG. 7 is a graph plotting ΔT versus nodularity.

The operator will have been previously supplied with a graph of $\Delta T$ versus nodularity as shown in FIG. 7. The graph of FIG. 7 has been established for typical nodular iron when poured into crucible 30. Changes in crucible design will require a new graph utilizing the principles disclosed herein. As shown in FIG. 7, the graph is preferably designated with zones such as green, yellow and red. When a $\Delta T$ falls in the green zone, one is certain that the iron has sufficient nodularity. If a $\Delta T$ falls in the yellow zone on the graph shown in FIG. 7, the iron may be satisfactory but is questionable and further examination is necessary. If the $\Delta T$ falls in the red zone on the graph shown in FIG. 7, the iron is certain to have insufficient nodularity.

When analyzing a specimen of cast iron, it is recommended that the cooling time starting with the casting of the sample and ending with solidification of portions 14 or 34 should not be less than 1½ minutes in order to prevent the formation of carbides. Furthermore, the total duration of the analysis should be no longer than 5 minutes in order for the method to produce economic advantages. With these goals in mind, the dimensions of the crucible 10 are preferably chosen to meet these goals. Thus, the crucible 10 is preferably made from foundry sand with a resinous material binder, and with the inner diameter of the crucible lower part 13 being between about 18.5 mm and the inner diameter of part 12 is about 50 mm.

If a single temperature sensing element is used in that portion of the crucible which cools the fastest, ΔT is obtained from a graph as shown in FIGS. 4 and 6. If the crucible has dual thermal couples as shown in FIG. 1, ΔT' is obtained off the graph shown in FIG. 3. Then, the ΔT' is used with a graph attained experimentally to ascertain nodularity.

Thus, the present invention comprehends obtaining a parameter of heat conductivity such as a ΔT after pouring a sample into a crucible and thereafter using the diameter to predict whether or not the nodularity of castings to be made from the entire ladle will be satisfactory whereby pouring can commence. If the nodularity is unsatisfactory, corrections may be made before the molten metal is poured or the entire ladle is pigged, thereby saving the molds and other operating costs. Nodularity can change with time. Hence, it may be desirable to use the present invention to check nodularity after all castings have been poured to confirm that the quality of the last poured castings.

When the present invention is used as part of an IN-MOLD process, a variety of variations are possible. For example, the main mold cavity could correspond to portion 36 of crucible 30 and portion 34 of the crucible 30 could be a small auxiliary cavity and arranged to cool at a faster rate. The casting resulting from the auxiliary cavity would be removed along with the sprue.

An electronic microprocessor or desk calculator may be interfaced with a digital pyrometer for use as computer analysis control equipment with red, yellow and green lights comparable to the zones of FIG. 7. The present invention will drastically reduce quality control problems and eliminate the cast of casting of molten metal with insufficient nodularity.

The present invention may be embodied in other specific forms without departing from the spirit or essential attributes thereof and, accordingly, reference should be made to the appended claims, rather than to the foregoing specification as indicating the scope of the invention.

It is claimed:

1. A process for predicting the metallographic structure of casting comprising:
    (a) obtaining a sample of molten metal,
    (b) cooling said sample,
    (c) ascertaining a parameter of thermal conductivity of the sample during step (b) and when thermal conductivity has a minimal influence as the cooling rate of the sample,
    (d) using said parameter of thermal conductivity to predict a metallographic structure of said casting.

2. A process in accordance with claim 1 wherein the metallographic structure is nodularity and the molten metal is cast iron.

3. A process in accordance with any one of claims 1 wherein step (c) includes causing a first part of the sample to solidify at a first rate and a second part of the sample at a second slower rate, and measuring the temperature of said first part of the sample.

4. A process in accordance with claim 3 wherein step (c) includes ascertaining the cooling rate of a portion of the sample in a temperature zone when thermal conductivity has a minimal influence on the cooling rate thereof and thereafter ascertaining the thermal effect on the subsequent cooling rate by the remaining portion of the sample over a fixed period of time.

5. A process in accordance with claim 3 wherein step (c) includes ascertaining the cooling rate of a portion of the sample in a temperature zone when thermal conductivity has a minimal influence on the cooling rate thereof and thereafter ascertaining the thermal effect on the subsequent cooling rate by the remaining portion of the sample over a predetermined temperature range.

6. A process in accordance with claim 1 wherein step (c) includes ascertaining the cooling rate of the sample in a temperature zone wherein thermal conductivity has a minimal influence on cooling rate.

7. A process in accordance with claim 4 or 6 wherein said zone includes the solidus temperature of the sample.

8. A process in accordance with claim 4 or 6 wherein said zone is approximately 100° C.

9. A process in accordance with claim 4 or 6 wherein the upper limit of said zone is about 1160° C. and the lower limit of said zone is about 1060° C.

10. A process in accordance with claim 1 wherein step (c) includes using temperature sensing means to determine differential cooling of portions of the sample.

11. A process in accordance with claim 10 wherein cooling is monitored over a period of time of about 3 minutes.

12. A process in accordance with claim 1 wherein step (a) includes pouring cast iron into a mold having a first cavity communicating with a second cavity, performing step (c) so that the sample is the cast iron in the first cavity, causing the sample in the first cavity to cool faster than the cast iron in the second cavity, performing step (d) to predict nodularity of the casting in the second cavity.

13. A process for predicting the nodularity of a casting made from molten nodular cast iron comprising:
    (a) pouring cast iron from a ladle into a crucible,
    (b) causing a first part of the cast iron to solidify in said crucible at a first rate and a second rate of the sample to solidify at a slower rate.
    (c) measuring at least the temperature of said first part during solidification thereof, and
    (d) using said temperature after solidification of the first part to determine nodularity of the cast iron sample in the crucible for predicting nodularity of castings to be made from the cast iron in the ladle.

14. Apparatus for use in determining a metallographic structure of molten metal comprising a crucible having a cavity therein, means for causing a first part of a sample in said cavity to cool at a faster rate than the second part of the sample, said means including said crucible which has two contiguous portions of said cavity with a smaller transverse dimension for said first part so that the ratio of surface area to volume of the second cavity part is smaller than that of said first cavity part, and temperature sensing means associated with said first part for measuring the temperature of a sample in said first part.

15. Apparatus in accordance with claim 14 wherein said first part is the only part of the cavity containing a temperature sensing means.

16. Apparatus in accordance with claim 14 wherein said crucible is a mold, said first cavity part being an auxiliary cavity to the main mold cavity which is said second part.

* * * * *